US00PP17312P2

(12) United States Plant Patent
Ackerman et al.

(10) Patent No.: US PP17,312 P2
(45) Date of Patent: Dec. 26, 2006

(54) STRAWBERRY PLANT NAMED 'PS-5016'

(50) Latin Name: *Fragaria ananassa*
Varietal Denomination: PS-5016

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 11/221,866

(22) Filed: Sep. 9, 2005

(51) Int. Cl.
*A01H 5/00* (2006.01)

(52) U.S. Cl. ..... Plt./208
(58) Field of Classification Search ..... Plt./208
See application file for complete search history.

(56) References Cited

U.S. PATENT DOCUMENTS

PP9,903 P * 5/1997 Ackerman et al. ..... Plt./209
PP10,686 P * 11/1998 Ackerman et al. ..... Plt./208
PP10,780 P * 2/1999 Ackerman et al. ..... Plt./208
PP11,110 P * 10/1999 Jamieson et al. ..... Plt./208

* cited by examiner

*Primary Examiner*—Wendy Haas
(74) *Attorney, Agent, or Firm*—Foley & Lardner LLP

(57) ABSTRACT

This invention relates to a new and distinct short-day variety of strawberry plant named 'PS-5016'. This new strawberry variety 'PS-5016' is primarily adapted to the growing conditions of the central coast of California, and is primarily characterized by its large plant size, vigorous growth rate with flowers visible above the plant for most of the year, large foliage size, light green in color and strongly concave in cross section, highly productive with fruit ripening beginning early, and produced fruit is small in size, medium red in color, conical in shape with excellent firmness, gloss and appearance.

4 Drawing Sheets

Latin name of the genus and species of the plant claimed: *Fragaria ananassa.*
Variety denomination: 'PS-5016'.

BACKGROUND OF THE INVENTION

The present invention relates to a new and distinct short-day strawberry variety designated as 'PS-5016'. This new variety is a result of a controlled cross made by the Inventors, Stephen M. Ackerman, Steven D. Nelson and Michael D. Nelson, in 1997 between strawberry variety designated 'PS-1150' (patented, U.S. Plant Pat. No. 10,780) and strawberry variety designated 'PS-1269' (patented, U.S. Plant Pat. No. 10,686). The variety is botanically known as *Fragria ananassa.*

The seedling resulting from the aforementioned cross was asexually propagated by stolons in a nursery located in Siskiyou County, Calif., and was subsequently selected by the Inventors from a controlled breeding plot near Salinas, Calif., in 1999. After its selection, the new variety was further asexually propagated by stolons in both Siskiyou County, Calif., and San Joaquin County, Calif. The new variety was extensively tested over the next several years in fruiting fields near Salinas, Calif. This propagation has demonstrated that the combination of traits disclosed herein as characterizing the new variety are fixed and remain true to type through successive generations of asexual reproduction.

BRIEF SUMMARY OF THE INVENTION

'PS-5016' is primarily adapted to the climate and growing conditions of the central coast of California. This region provides the necessary winter temperatures required for it to produce a strong vigorous plant and to remain in fruit production from April through November. The nearby Pacific Ocean provides the needed humidity and moderate temperatures to maintain fruit quality during the spring, summer and fall production months.

The following traits have been repeatedly observed and are determined to be unique characteristics of 'PS-5016', which in combination distinguish this strawberry plant as a new and distinct variety:

1. large plant size;
2. vigorous growth rate with flowers visible above the plant for most of the year;
3. large foliage size, light green in color and strongly concave in cross section;
4. highly productive with fruit ripening beginning early; and
5. produced fruit is small in size, medium red in color conical in shape with excellent firmness, gloss and appearance.

The strawberry varieties that are believed to be most closely related to the new strawberry variety 'PS-5016' are the strawberry variety 'PS-592' (patented, U.S. Plant Pat. No. 9,903) and the parental strawberry variety 'PS-1150'.

In comparison to the similar strawberry varieties 'PS-592' and 'PS-1150', 'PS-5016' differs by the following combination of characteristics as described in Table 1:

TABLE 1

| Characteristic | 'PS-5016' | 'PS-592' (PP9,903) | 'PS-1150' (PP10,780) |
|---|---|---|---|
| Plant | | | |
| Size | large | large | medium-small |
| Stolon anthocyanin coloration | medium-strong | medium-weak | medium-strong |
| Foliage/Petioles | | | |
| Leaf color | light green | medium green | medium green |
| Leaf size | large | large | small |
| Shape in cross section | slightly-strongly concave | slightly concave | slightly concave-flat |
| Blistering | medium-strong | medium-strong | medium-weak |
| Stipule length | medium | long | medium |
| Fruit | | | |
| Size | small | large | small |
| Flavor | very good | very good | good |
| Color | red | red-orange red | red |
| Attitude of calyx segments | spreading-collapsing | spreading-reflexed | spreading-collapsing |
| Skin firmness | strong | medium | strong |
| Inflorescences | | | |
| Position relative to foliage | above | level with to below | above |
| Fruiting truss length | long | long | medium |
| Time of ripening | early | early | late |

For identification, a series of molecular markers have been determined for this new variety.

BRIEF DESCRIPTIONS OF THE DRAWINGS

The accompanying color photographs illustrate the overall appearance of typical specimens of the new strawberry variety 'PS-5016' at various stages of development as true as reasonably possible with color reproductions of this type. Color in the photographs may differ slightly from the color value cited in the detailed botanical description which accurately describe the color of 'PS-5016'. The depicted plant and plant parts of the new strawberry variety 'PS-5016' were taken in Salinas, Calif., and are approximately 8 to 9 months old.

DETAILED BOTANICAL DESCRIPTION

Figure 1:
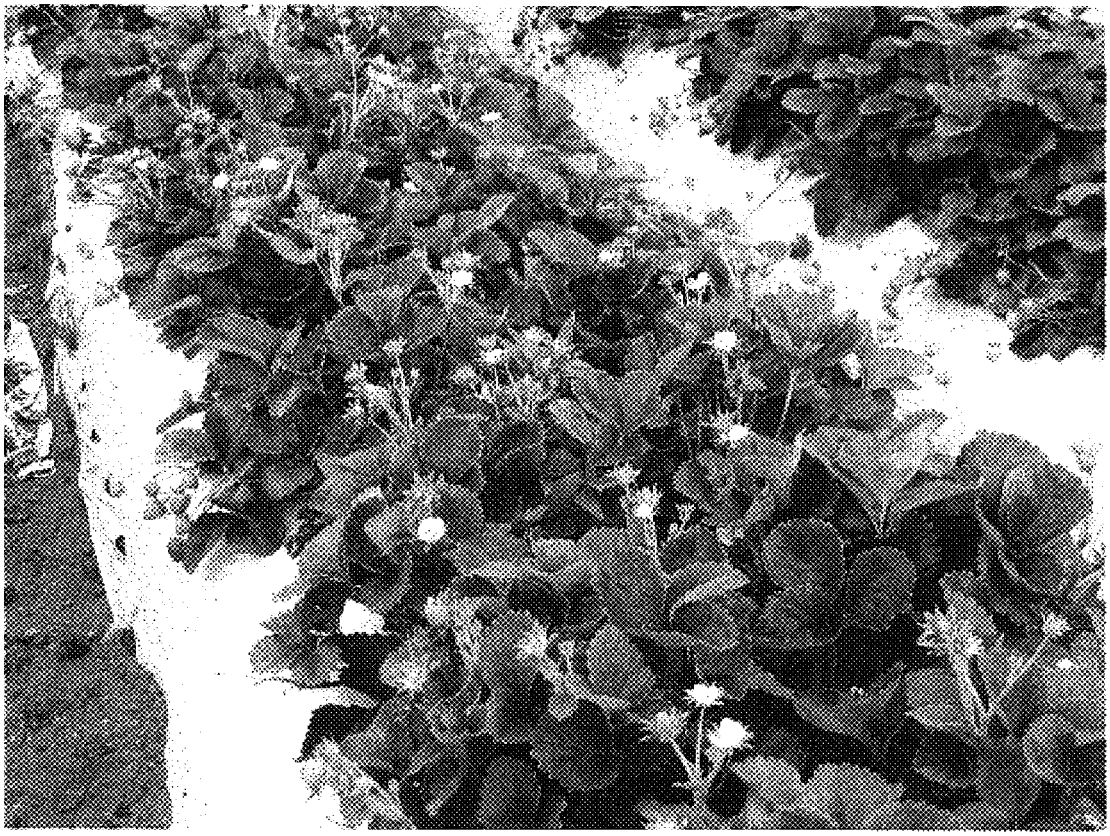
FIG. 1 shows typical fruiting field characteristics on Jun. 11, 2004.
Figure 2:
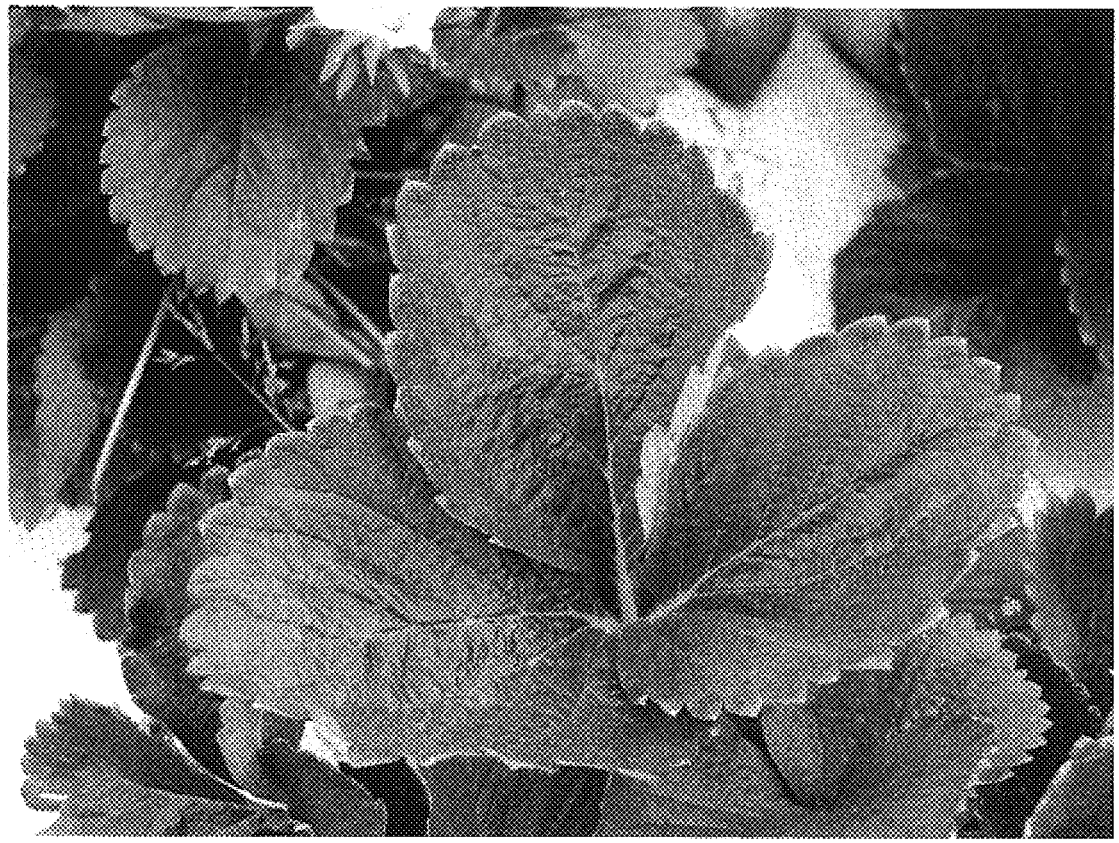
FIG. 2 shows a close-up view of a typical mature trifoliate on Jun. 3, 2004.
Figure 3:
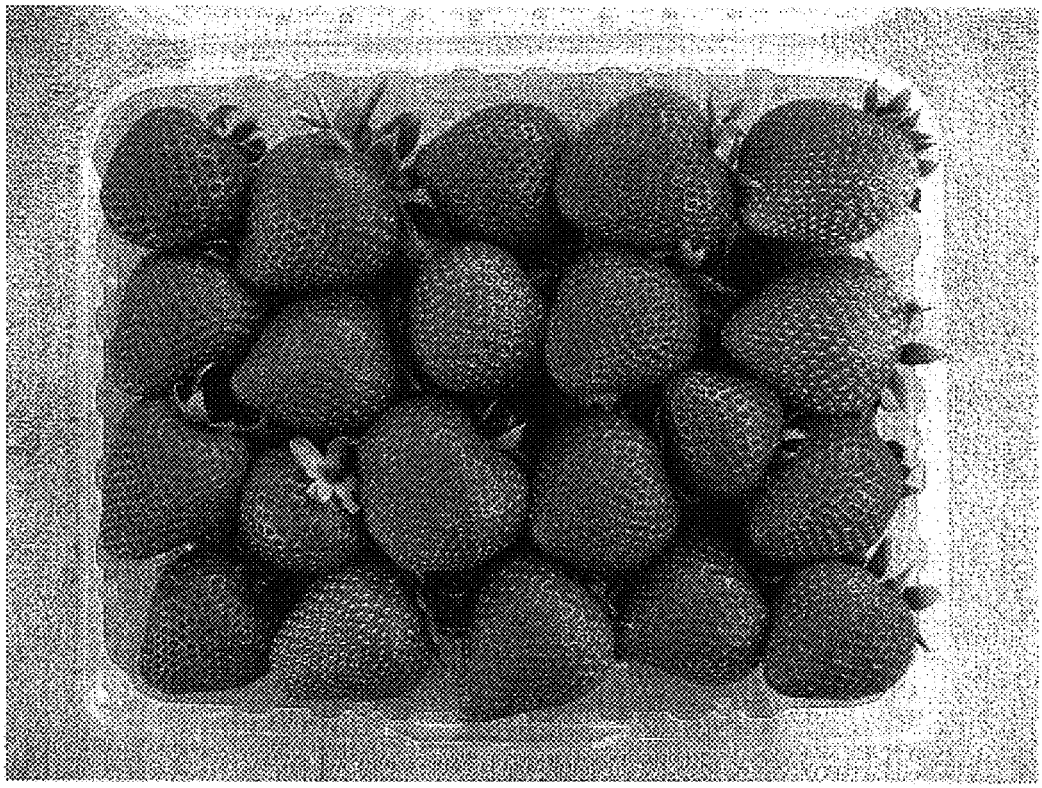
FIG. 3 shows a close-up view of fruit on Jul. 12, 2004.
Figure 4:
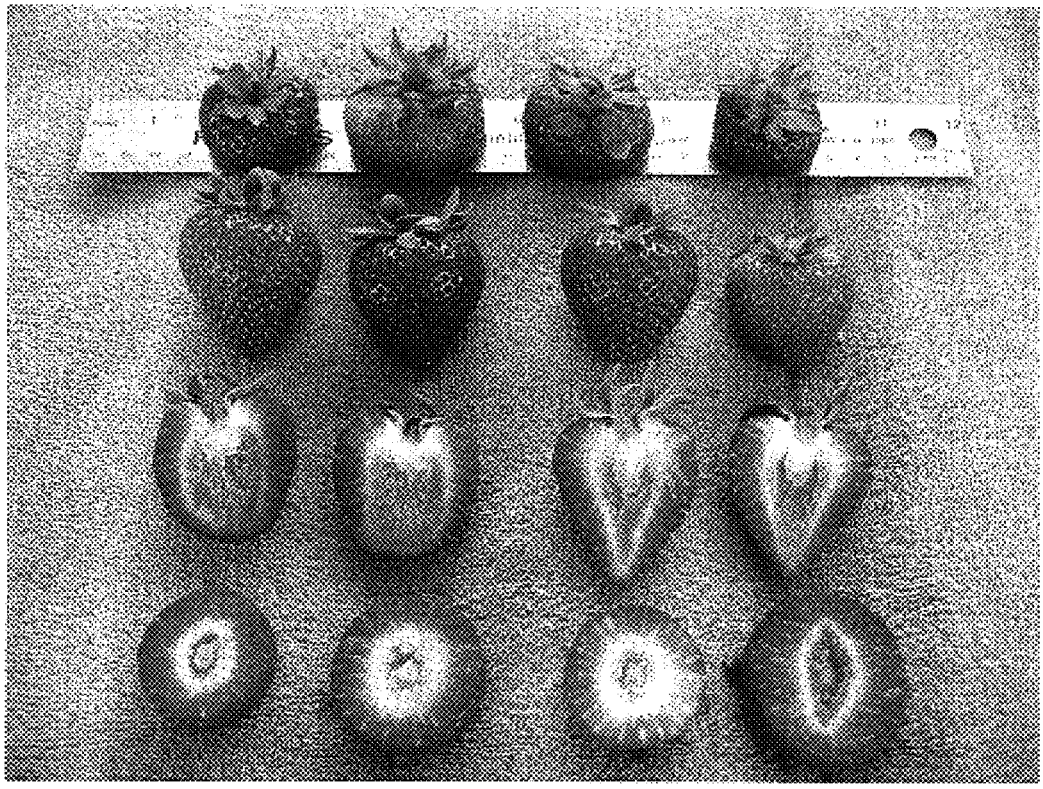
FIG. 4 shows typical internal and external fruit characteristics on Jul. 16, 2004.
Figure 5:
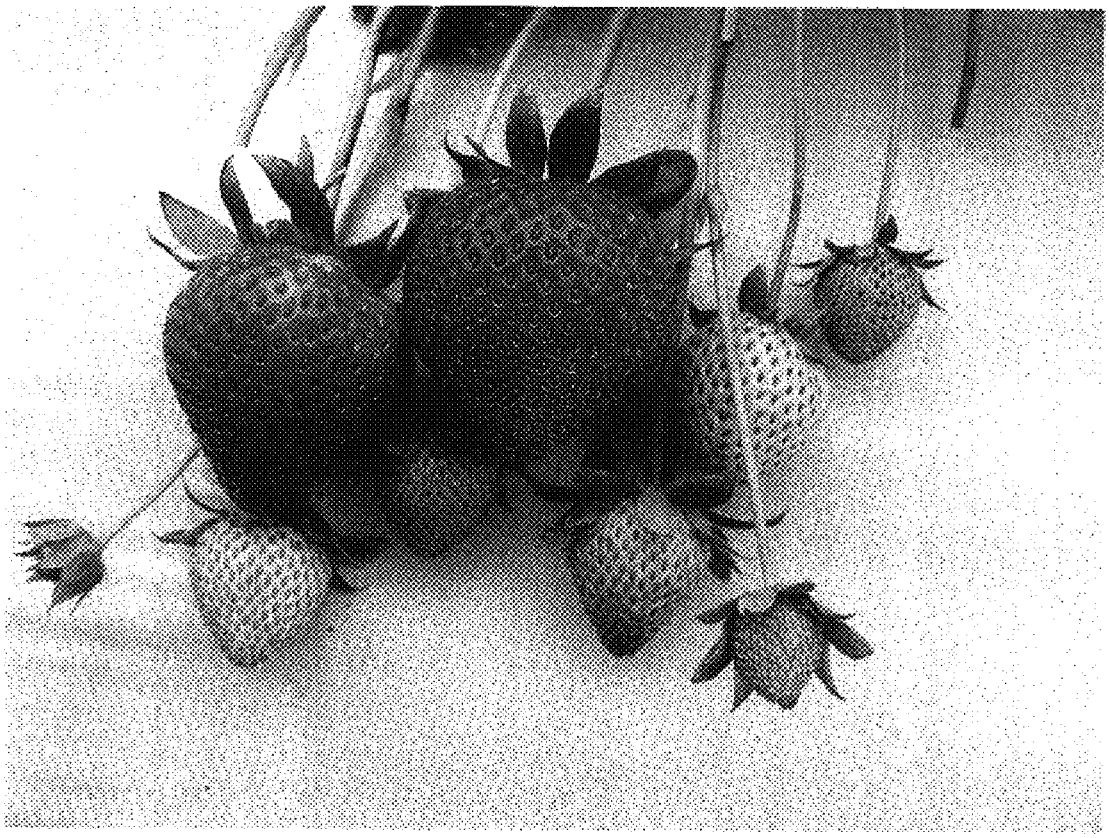
FIG. 5 shows typical mature and immature field fruit on Jun. 3, 2004.

'PS-5016' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new strawberry variety 'PS-5016', unless otherwise noted, is based on observations taken during the 2004 growing season in Salinas, Calif. These measurements and ratings were taken from plants of 'PS-5016' dug from a high-elevation nursery located in Siskiyou County, Calif., during the middle of October 2003 and planted approximately 3 weeks later in Salinas, Calif. The approximate age of the observed plants is 8 to 9 months. Yield observations and fruit quality characterisitcs are averaged from three years of data collected from the 2002 through the 2004 growing seasons.

Color terminology follows the Munsell Book of Colors, Munsell Color, Baltimore, Md. (1976).

Fruit characteristics: Tables 2, 3 and 4 describe fruit, fruit production and fruit quality characteristics of 'PS-5016'. Fruit characteristics are taken from secondary fruit on a first year planting.

CHART 1

| | 'Poulpar038' | 'Poulra024' |
|---|---|---|
| Petal count | 35 to 40 | 31 |
| Flower diameter | 65 to 75 mm | 45 to 50 mm |
| General tonality of flower color | Red-Purple N57 B | Red 52 C |

| | |
|---|---|
| c-1: | Ethylene glycol di(meth)acrylate |
| c-2: | Diethylene glycol di(meth)acrylate |
| c-3: | Triethylene glycol di(meth)acrylate |
| c-4: | Polyethylene glycol di(meth)acrylate (number average molecular weight: 150–1000) |
| c-5: | Propylene glycol glycol di(meth)acrylate |
| c-6: | Dipropylene glycol di(meth)acrylate |
| c-7: | Tripropylene glycol di(meth)acrylate |
| c-8: | Polypropylene glycol di(meth)acrylate (number average molecular weight: 200–1000) |
| c-9: | Neopentyl glycol di(meth)acrylate |
| c-10: | 1,3-Butanediol glycol di(meth)acrylate |
| c-11: | 1,4-Butanediol glycol di(meth)acrylate |
| c-12: | 1,6-Hexanediol glycol di(meth)acrylate |
| c-13: | Hydroxypivalic ester neopentyl glycol di(meth)acrylate |
| c-14: | Bisphenol A glycol di(meth)acrylate |
| c-15: | Trimethylolpropane tri(meth)acrylate |
| c-16: | Pentaerythritol tri(meth)acrylate |
| c-17: | Dipentaerythritol hexa(meth)acrylate |
| c-18: | Pentaerythritol tetra(meth)acrylate |
| c-19: | Trimethylolpropane di(meth)acrylate |
| c-20: | Dipentaerythritol monohydroxypenta(meth)acrylate |

TABLE 4

Comparison of secondary fruit characteristics of 'PS-5016', with standards from Salinas, California, Jul. 13, 2004.

| Character | 'PS-5016' | 'PS-592' | 'PS-1150' |
|---|---|---|---|
| Munsell Color Range Mature Fruit | 7.5R 3/10 to 7.5R 4/10 | 7.5R 3/12 to 7.5R 4/12 | 7.5R 4/10 to 7.5R 3/8 |
| Fruit Length mean (cm) | 3.9 | 4.7 | 4.1 |
| Fruit Width mean (cm) | 3.8 | 4.5 | 3.8 |
| Fruit Length/Width Ratio | 1.03 | 1.04 | 1.09 |
| Calyx Diameter mean (cm) | 4.3 | 4.7 | 4.4 |
| No. Sepals/Berry | 14.7 | 13.3 | 12.9 |

Fruit:

*Ratio of length to width.*—As long as broad to slightly longer than broad.

*Size.*—Medium.

*Predominant shape.*—Conical.

*Difference in shapes between primary and secondary fruit.*—None to very slight.

*Band without achenes.*—Absent or very narrow.

*Unevenness of surface.*—Absent or very weak.

*Color of mature fruit.*—Red, (7.5R 3/10 to 7.5R 4/10).
*Evenness of color.*—Even.
*Glossiness.*—Medium.
*Insertion of achenes.*—Level with surface.
*Insertion of calyx.*—In basin to level with.
*Attitude of the calyx segments.*—Spreading to collapsing.
*Size of calyx in relation to fruit diameter.*—Slightly larger.
*Adherence of calyx* (*when fully ripe*).—Strong.
*Firmness of skin.*—Medium to strong.
*Firmness of flesh.*—Medium to firm.
*Color of flesh.*—Medium red (7.5R 4/10 to 7.5R 4/12).
*Distribution of red color of the flesh.*—Marginal and central.
*Hollow center.*—Moderately expressed.
*Receptacle color.*—Whitish (N 9.25/84.2%R to N 9/78.7%R).
*Seed color.*—Moderate red to moderate yellow (7.5R 3/8 to 5Y 6/8).
*Seed size.*—Small (average 0.53 mg).
*Time of flowering* (*50% of plants at first flower*).—Early.
*Time of ripening* (*50% of plants with ripe fruit*).—Early.
*Type of bearing.*—Not remontant.

Plant characteristics: Table 5 describes plant characteristics of 'PS-5016'. Plant characteristics are taken from a fully mature mid season plant.

TABLE 1

| Characteristic | 'Kakegawa S80' | '9B-58C' | '7BC-42A-1' |
|---|---|---|---|
| Flower color | Blue with deep blue veins | Red | Dark orange |
| Growth habit | Semi-creeping | Semi-creeping | Semi-erect |

Plant:

*Size.*—Large.
*Habit.*—Globose.
*Density.*—Medium.
*Vigor.*—Strong.
*Stolons.*—Number: Medium to few. Anthocyanin coloration: Weak (7.5R 5/6 to 7.5R 6/6). Thickness: Thin. Pubescence: Medium to strong.

Foliage characteristics: Table 6 describes foliage characteristics of 'PS-5016'. Foliage characteristics are taken from a fully mature tri-foliate during mid season.

TABLE 1

| SN. | RADIUS | THICKNESS | GLASS | CLR. AP. |
|---|---|---|---|---|
| 1 | 100.8190 | 6.00000 | ACRYLIC | 107.63 |
| 2 | 48.9744 | 15.25518 | | 84.97 |
| 3a | 143.9044 | 6.00000 | ACRYLIC | 81.86 |
| 4a | 43.3618 | 37.93520 | | 68.93 |
| 5a | 35.6345 | 15.00000 | STYRENE | 54.27 |
| 6a | 81.6110 | 17.36272 | | 47.86 |
| 7 | Aperature stop | 7.77990 | | 37.45 |
| 8a | −27.2425 | 6.00000 | STYRENE | 37.38 |
| 9a | −423.3710 | 0.50000 | | 45.18 |
| 10 | 107.7346 | 15.00000 | SK5 | 52.75 |
| 11 | −73.4827 | 4.00000 | SP6 | 57.31 |
| 12 | −1002.5660 | 1.50000 | | 64.58 |
| 13 | 108.4138 | 23.00000 | SK5 | 80.44 |
| 14 | −95.4279 | 0.50000 | | 82.81 |
| 15a | 133.2972 | 12.00000 | ACRYLIC | 84.41 |
| 16a | −132.2276 | 114.48260 | | 83.83 |
| 17a | 139.3172 | 15.00000 | ACRYLIC | 108.80 |
| 18a | −700.0000 | 10.00020 | | 108.50 |

EVEN POLYNOMIAL ASPHERES

| SN. | AD | AE | AF | AG | AH | AI |
|---|---|---|---|---|---|---|
| 1 | −1.5934E-07 | −3.2301E-11 | −8.4041E-15 | −1.4417E-18 | 1.0816E-22 | 2.0851E-25 |
| 3 | 2.0545E-06 | −1.5307E-10 | 1.8192E-13 | 7.9530E-17 | 2.8673E-20 | 1.1986E-23 |
| 4 | −9.7451E-08 | 4.9263E-10 | −4.9311E-13 | 2.6150E-16 | 3.9054E-19 | 1.2880E-22 |
| 5 | −2.3574E-07 | −1.3342E-09 | 5.3174E-12 | −7.7048E-17 | −1.1073E-17 | 1.2716E-20 |
| 6 | −8.2802E-07 | 1.6251E-09 | 1.1805E-12 | −2.0627E-14 | 5.0501E-17 | −3.3873E-20 |
| 8 | 4.4580E-07 | −4.4341E-09 | 1.5629E-11 | 9.3004E-15 | −1.6550E-16 | 2.5239E-19 |
| 9 | 8.5180E-07 | −1.8891E-10 | 1.2699E-12 | 5.1184E-16 | −2.8733E-18 | 3.3000E-21 |
| 15 | −1.6675E-07 | 8.4927E-11 | 3.6771E-14 | 2.5463E-17 | −5.0093E-21 | −1.1761E-23 |
| 16 | 1.7020E-06 | 2.7211E-10 | 3.2080E-14 | 3.7396E-17 | −1.0735E-20 | −7.5127E-24 |
| 17 | −1.8602E-07 | 5.2861E-11 | −2.2361E-14 | 5.1543E-18 | −1.9417E-21 | 4.4279E-25 |

SYSTEM FIRST ORDER PROPERTIES

| | | |
|---|---|---|
| OBJ. HT: −660.40 | fl: 2.40 | MAG: −0.0800 |
| EFL: 65.6056 | FVD: 307.316 | ENP: 57.7119 |
| IMD: 10.0002 | BRL: 297.316 | EXP: −13189.8 |
| OBD: −762.684 | OVL: 1070.00 | |
| STOP: 0.00 after surface 7. DIA: 37.446 | | |

Foliage:

*Color of upper surface.*—Medium green, (7.5GY 3/4 to 7.5GY 3/6).

*Color of under side.*—Medium grey green, (5GY 5/4 to 5GY 6/4).

*Shape in cross section.*—Slightly concave to strongly concave.

*Blistering.*—Medium to strong.

*Glossiness.*—Medium.

*Number of leaflets/leaf.*—Three.

*Terminal leaflet.*—Size: Large. Length/width ratio: As long as broad to longer than broad. Shape of base: Obtuse. Shape of incision of margins: Obtuse.

*Petiole.*—Pubescence: Moderate.

*Anthocyanin coloration of stipule.*—Medium.

*Attitude of hairs.*—Slightly outwards to upwards.

*Frequency of bract leaflets.*—Some (50–60%).

Flowers and inflorescences: Table 7 describes inflorescence and flower characteristics of 'PS-5016'. Inflorescence characteristics are taken from a fully mature plant while flower characteristics are taken from a secondary flower during mid season.

Inflorescence:

*Position relative to foliage.*—Above.

*Pubescence.*—Strong.

*Anthocyanins.*—Moderate.

*Number of bract leaflets.*—Bracts occur on about 90% of the inflorescences.

*Size of bract leaflets.*—Large.

*Fruiting truss length.*—36.0 cm.

Flowers:

*Color.*—White (N9.5/90.0%R to N9.25/84.2%R).

*Size.*—Medium.

*Size of calyx relative to corolla.*—Larger.

*Relative position of petals.*—Overlapping.

*Petal length/width ratio.*—As long as broad to longer than broad.

Pest reactions: This new variety may not be resistant to any of the known insects, diseases or viruses common in California. It is known to be tolerant to the two-spotted spider mite, aphid and flower thrips when treated properly. It is also known to be moderately tolerant to grey fruit mold, yet susceptible to powdery mildew and angular leaf spot. The susceptibility of the new variety to any of the virus complexes of California has not been determined.

TABLE 2

| SN. | RADIUS | THICKNESS | GLASS | CLR. AP. |
|---|---|---|---|---|
| 1 | 158.7994 | 8.37562 | BK7 | 95.61 |
| 2 | 38.8752 | 32.61261 | | 69.13 |
| 3a | 94.7110 | 12.00000 | STYRENE | 63.03 |
| 4 | −203.5070 | 0.27919 | | 61.22 |
| 5a | 42.9601 | 7.44470 | ACRYLIC | 46.52 |
| 6a | 29.5212 | 27.52002 | | 36.41 |
| 7a | −29.5212 | 7.44470 | ACRYLIC | 38.06 |
| 8a | −42.9601 | 0.27919 | | 47.24 |
| 9 | −95.0201 | 4.18781 | SF14 | 52.65 |
| 10 | 153.0600 | 18.61174 | SK5 | 63.41 |
| 11 | −40.9609 | 0.27919 | | 63.59 |
| 12a | −1496.9570 | 15.00000 | ACRYLIC | 73.63 |
| 13 | −76.4720 | 105.36350 | | 76.70 |
| 14a | 104.2866 | 18.00000 | ACRYLIC | 107.94 |
| 15 | −535.3889 | 9.99825 | | 107.71 |

EVEN POLYNOMIAL ASPHERES

| SN. | AD | AE | AF | AG | AH | AI |
|---|---|---|---|---|---|---|
| 3 | 1.2971E-06 | −1.9595E-10 | 9.6038E-14 | 5.3556E-17 | −9.0228E-20 | 1.3068E-22 |
| 5 | 1.8328E-06 | −4.7943E-10 | 1.1410E-11 | −1.3831E-14 | 2.0351E-17 | −1.7888E-21 |
| 6 | 2.7335E-06 | 1.3736E-08 | −3.3516E-11 | 1.0660E-13 | −8.6134E-17 | 2.6188E-19 |
| 7 | −2.7335E-06 | −1.3736E-08 | 3.3516E-11 | −1.0660E-13 | 8.6134E-17 | −2.6188E-19 |
| 8 | −1.8328E-06 | 4.7913E-10 | −1.1410E-11 | 1.3831E-14 | −2.0351E-17 | 1.7888E-21 |
| 12 | −1.7503E-08 | −5.9870E-10 | 5.5361E-13 | −1.0091E-16 | −2.0521E-19 | 9.6568E-23 |
| 14 | −6.5592E-07 | −3.0849E-10 | 3.2824E-13 | −1.1758E-16 | 1.9238E-20 | −1.1976E-24 |

SYSTEM FIRST ORDER PROPERTIES

| | | |
|---|---|---|
| OBJ. HT: −660.40 | fl: 2.40 | MAG: −0.0800 |
| EFL: 65.9995 | FVD: 267.397 | ENP: 47.5474 |
| IMD: 9.99825 | BRL: 257.398 | EXP: 933.924 |
| OBD: −772.750 | OVL: 1040.15 | |
| STOP: 13.76 after surface 6. DIA: 34.222 | | |

We claim:

1. A new and distinct strawberry plant named 'PS-5016', as herein described and illustrated by the characteristics set forth above.

* * * * *